United States Patent

Garrity et al.

[11] Patent Number: 6,045,821
[45] Date of Patent: *Apr. 4, 2000

[54] LIPOSOMAL AGENTS

[75] Inventors: Martha Garrity; John Varadarajan; Alan David Watson, all of Wayne, Pa.

[73] Assignee: Nycomed Salutar, Inc., Wayne, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/809,729

[22] PCT Filed: Oct. 9, 1995

[86] PCT No.: PCT/GB95/02378

§ 371 Date: May 29, 1997

§ 102(e) Date: May 29, 1997

[87] PCT Pub. No.: WO96/11023

PCT Pub. Date: Apr. 18, 1996

[30] Foreign Application Priority Data

Oct. 10, 1994 [GB] United Kingdom ............ 9420390

[51] Int. Cl.⁷ .................................. A61K 9/127
[52] U.S. Cl. ............ 424/450; 424/1.21; 424/9.321; 424/9.51; 424/9.3; 424/9.361; 424/9.42
[58] Field of Search ............... 424/450, 9.321, 424/1.21, 9.3, 9.323, 9.51, 9.322, 9.36, 9.361, 9.42

[56] References Cited

U.S. PATENT DOCUMENTS

| | | |
|---|---|---|
| 4,603,044 | 7/1986 | Geho et al. |
| 5,053,503 | 10/1991 | Dean et al. .......... 540/474 |
| 5,534,241 | 7/1996 | Torchilin et al. .......... 424/9.321 |

FOREIGN PATENT DOCUMENTS

| | | |
|---|---|---|
| 0 572 049 | 12/1993 | European Pat. Off. . |
| WO89/09625 | 10/1989 | WIPO . |
| WO91/14460 | 10/1991 | WIPO . |
| WO-92/21017 | 11/1992 | WIPO . |
| WO92/21384 | 12/1992 | WIPO . |
| WO-95/24255 | 9/1995 | WIPO . |
| WO-95/28392 | 10/1995 | WIPO . |

OTHER PUBLICATIONS

Angew, Chem. Int. Ed. Eng. 30: 567–658 (1991).
Ann. N.Y. Acad. Sci., 698: 427–43 (1993).
Carroll J. Med. Chem., 29 1821–1826 (1996).
Dancey, J. Immunol 122: 638 (1979).
DTPA–stearyl esters of Tilcock et al. Mag. Res. Med. 27: 44–51 (1992).
Dumont, Tetrahedron Lett. 33(22), 3707.
Gregoriades, Biochem Soc. Trans. 17: 128 (1989).
Hnatowich et al. J. Nucl. Med 22: 810–814 (1981).
Johnston, Liposome Technology, vol. 1, Gregoriades Ed., pp. 123–129 (1983).
Jones, Adv. Drug. Deliv. 13: 215–250 (1994).
Karlik et al. Mag. Res. Med. 19: 56–66 (1991).
Kinsky, Biochim Biophs Acta 769: 543 (1984).
Kosewer, JACS, 78: 4347–4355 (1956).
Kung, Biochim Biophys Acta 862: 435–439 (1986).
Papahadjopolous: Biochim. Biophys. Acta. 1103: 185–197 (1992).
Santaella, FEBS Letters 336: 481–484 (1993).
Singh, Phospholipid Handbook, Cevc Ed., Dekker, pp. 233–291 (1993).
Torchillin, Phospholipid Handbook, Marcel Dekker, Inc., G. Cevc, ed., Chapter 8.
Weissig, Biochim Biophs Acta 1003: 54–57 (1989).
Torchilin, et al., *Journal of Controlled Release*, vol. 28, No. 1/03, Jan. 1, 1994, pp. 45–58.
Krause et al., *Journal of Liposome Research*, vol. 5, No. 1, Feb. 1, 1995, pp. 1–26.
Tilcock, J. Liposome Res. (1994), 4(2), 909–36.
Trubetskoy et al., *J. Liposome Res.* (1994), 4(2), 961–80.
Tilcock et al., *Database Chemabs*, Chemical Abstracts Service, Columbus, Ohio, US, AN=117:229262, 1992.
Ahkong et al., *Database Chemabs*, Chemical Abstracts Service, Columbus, Ohio, US, AN=118:76261, 1992.
Tilcock et al., *Magnetic Resonance in Medicine*, vol. 27, No. 1, Sep. 1992, pp. 44–51.
Buck, *Journal of Nuclear Medicine*, vol. 17, No. 12, Dec. 1977, pp. 1102–1103.

Primary Examiner—Gollamudi S. Kishore
Attorney, Agent, or Firm—Bacon & Thomas

[57] ABSTRACT

The present invention relates to a liposomal agent comprising liposomes having bound to a membrane thereof a chelated diagnostically or therapeutically effective metal ion. The chelating agent binding the metal ion has a macrocyclic chelant moiety with, attached to a single ring atom thereof, a lipophilic membrane associating moiety.

16 Claims, No Drawings

LIPOSOMAL AGENTS

This application is a 371 of PCT/GB95/02378 Oct. 9, 1995.

This invention relates to novel liposomal agents, in particular parenterally administrable agents having membrane bound macrocyclic chelant groups which carry diagnostically or therapeutically useful metal ions. Such liposomal agents may be used in therapy or as contrast enhancing agents in diagnostic imaging modalities such as MRI, scintigraphy, X-ray and CT.

The use of diagnostic agents in medical imaging procedures is well established.

In MRI, contrast agents generally derive their contrast enhancing effect from the inclusion of a material exhibiting paramagnetic, ferrimagnetic, ferromagnetic or superparamagnetic behaviour, eg. a chelated paramagnetic metal ion (such as Gd or Dy) or an iron oxide nanoparticle. These materials affect the characteristic relaxation times of the imaging nuclei in the body regions into which they distribute causing an increase or decrease in MR signal intensity.

In X-ray and CT, contrast agents derive their effect from their ability to alter the X-ray transmission characteristics of the body regions into which they distribute and as a result the use of chelated heavy metal ions, which have large X-ray cross sections, as X-ray contrast agents has been proposed.

In scintigraphy, the imaging agent is a radionuclide, eg. a chelated radioactive metal ion, generally a gamma emitter.

For therapy, the use of chelated metal species, either radionuclides or metals which themselves have a therapeutic effect, such as vanadium for diabetes therapy, is also well known.

While therapeutically and diagnostically useful metal chelates have long been used in medicine, there does remain a need for metal chelate based agents with improved biodistribution and bioelimination profiles. On parenteral administration, simple water soluble low molecular weight metal chelates, such as the MRI contrast agents GdDTPA and GdDTPA-BMA, distribute throughout the extracellular fluid (ECF) without any particular site specificity and are rapidly excreted through the kidneys by glomerular filtration. Other agents have been proposed which, due to their particulate or lipophilic nature are rapidly abstracted from the blood by the reticuloendothelial (RES) system or by liver hepatocytes and thus are suitable as hepatobiliary agents.

One approach to the development of a blood pool agent, ie. an agent which remains within the vascular space for an extended period sufficient to expand the time available for imaging, has been to use water-soluble polychelate macromolecules with molecular weights above the kidney threshold. Another approach in the effort to develop site-specific agents has been to couple chelates, eg. monochelates, oligochelates or polychelates, to a site directed molecule, usually a macromolecule. Thus for example gadolinium chelates have been coupled to albumin and immunoglobulins. There are however several drawbacks to this approach. A large number of chelated metal ions per macrostructure is required. Where a large number of chelates are coupled to a site-directed molecule, its site-specificity may be reduced. Controlling the preparation processes to give reproducible metal loading levels, homogeneous products and high target specificity is difficult and such processes are costly. The excretion and metabolic pathways for such agents are complex and not well understood. The scientific study and documentation required to trace all potential metabolites produced by RES elimination would be extensive. It is thus not surprising that, to date, there are no macromolecular gadolinium based contrast agents in clinical trials.

Since injected particulates are rapidly taken up by the RES, the use of liposomal contrast agents has also been widely suggested.

Liposomes, the term is used herein to refer to particles having one or more encapsulating membranes formed by amphiphilic molecules (such as lipids for example) and in particular particles having a bilayer membrane and an enclosed aqueous core, are versatile carriers for the site specific delivery of therapeutic and diagnostic agents. They can be used to selectively target specific organs, such as the liver, spleen, lung, lymphatic system, and bone marrow or they can be retained in the vasculature.

The composition and size of liposomal agents can be selected to control their biodistribution and, since one can use as the bulk of the membrane-forming molecules naturally occurring phospholipids, their metabolization and metabolite elimination can pose far fewer problems than is the case with macromolecular reagents.

Liposomal agents generally fall into two categories: a first where the liposome is used to entrap a desired therapeutic or diagnostic agent within the central aqueous cavity; and a second where the desired entity is tethered to the liposomal membrane as a result of its including a hydrophobic "anchor" group which becomes incorporated into the membrane. Both forms have been suggested in relation to imaging agents.

The present invention is concerned with liposomal agents in which metal chelate moieties are tethered to the liposomal membrane.

Membrane tethered chelates previously suggested have generally involved linear chelant groups, such as DTPA, with one or two of the chelating functions derivatised to attach to lipophilic anchor groups. Examples include the dipalmitoylphosphatidylethanolamine (PE): DTPA-anhydride chelants of Karlik et al. (see Mag. Res. Med. 19: 56–66 (1991)), the DTPA-distearylamides of Hnatowich et al. (see J. Nucl. Med. 22: 810–814 (1981)), the DTPA-stearyl esters of Tilcock et al. (see Mag. Res. Med. 27: 44–51 (1992)) and the various twin lipophilic group carrying chelants of Unger et al. (see WO-92/21017).

Besides linear chelants carrying twin lipophilic anchor groups, Unger (supra) also suggested the use of N4 macrocyclic chelants carrying lipophilic groups on two opposed ring nitrogens. The synthetic route described to prepare the twin anchored chelate results in a mixture of products not the 1,7-diamide reported. A synthetic route to the 1,7-di-substituted isomer would be much more complicated. For example, the method described by Dumont (Tetrahedron Lett. 35(22), 3707). Furthermore, the chelating efficacy is severely prejudiced. Since liposomes are cleared from the body by the RES whereby they are exposed to the acidic environment within liver cells, highly stable complexes are necessary to avoid long term retention of gadolinium. We have found that metal elimination is optimized by the use of membrane bound macrocyclic chelant moieties having a lipophilic anchor group attached at only one ring atom.

We have thus found that metal utilization and elimination are optimised by the use of membrane bound macrocyclic chelant moieties having a lipophilic anchor group attached at only one ring atom, the macrocyclic chelant and anchor groups preferably being coupled to each other, advantageously via a biodegradable bond, after liposome formation.

Viewed from one aspect therefore the invention provides a liposomal agent comprising liposomes having bound to a membrane thereof a chelated diagnostically or therapeutically effective metal ion, the chelating agent binding said metal ion having a macrocyclic chelant moiety with attached to a single ring atom thereof a lipophilic membrane associating moiety.

As a further aspect, the invention also provides a composition comprising a liposome membrane forming compound and a contrast enhancing compound the latter comprising a macrocyclic chelant moiety with attached to a single ring atom thereof a lipophilic membrane associating moiety, from which liposomal compositions may be produced.

The invention is particularly important in that it provides for liposome compositions with enhanced elimination of the contrast enhancing component from the liver. Eventually liposomes are recognized by the RES, taken up into cells by phagocytosis and deposited in the liver. The mechanisms whereby the chelates are cleared from the liver are not well understood. Water insoluble, hydrophobic materials such as GdDTPA-SA remain in the liver indefinitely. Most water soluble complexes have an elimination half-life from the liver of 6–8 days. We have found, however, that incorporation of certain moieties in the structure of the contrast agent accelerates the elimination from the liver. For example, gadolinium chelates with phenyl ring have improved elimination from the liver over simple aliphatic complexes. Further improvement in the elimination can be accomplished by the presence of one or more ionizable groups (such as carboxylate or sulfonate) on a phenyl ring. The elimination enhancing group can be incorporated into the structure of the contrast agent in the form of an anchoring group, a linking group or as the biodegradation product of an anchoring or linking group.

The macrocyclic chelate moiety in the contrast enhancing compound is preferably hydrophilic and is optionally electrostatically charged when in situ in the liposomes. As a result the chelate moiety will be positioned outside the lipid layer or layers of the liposomal membrane. While the invention allows for the chelate to be positioned outside the liposomal membrane or within the aqueous liposomal core volume, it is especially preferred that the chelate moiety be positioned preferentially, predominantly or substantially entirely on the exterior of the liposomes. This is particularly the case where the chelated species is intended to function as a positive, $T_1$-MR contrast agent.

Viewed from a further aspect, the invention provides a process for the preparation of a liposomal contrast agent according to the invention, said process comprising one of the following steps: (a) transforming a composition comprising an aqueous carrier medium, a liposomal membrane forming compound and an optionally metallated macrocyclic chelant compound having a hydrophobic membrane associating group attached at one macrocycle ring atom, into a liposomal composition and if required thereafter metallating said chelant compound; and (b) coupling an optionally metallated macrocyclic chelant compound to an anchor compound having a hydrophobic moiety incorporated within a liposomal membrane of a liposome and if required thereafter metallating said chelant compound.

Liposome formation and chelant metallation may be effected by conventional means as discussed further below and chelant:anchor coupling may also be effected by conventional coupling reactions using appropriately functionalized, and if desired activated, chelant and anchor compounds, optionally together with a bifunctional linking agent.

The liposomal contrast agent compositions of the invention may be used in diagnostic imaging procedures and thus in a further aspect the invention also provides a method of generating an enhanced image of a human or non-human, preferably mammalian, body, involving the parenteral administration to said body, in particular administration into the systemic vasculature, of a contrast agent and the generation of an image of at least part of said body, the improvement comprising administering as said agent a liposomal agent according to the invention.

Viewed from a still further aspect the invention also provides the use of a macrocyclic chelant or a chelate or salt thereof for the manufacture of a liposomal contrast agent according to the invention for use in diagnostic imaging.

Since it is well established that biotolerable liposomes can be produced, and since in vivo liposomal contrast agents according to the invention would biodegrade simply to the liposome components (the membrane and core-forming species) and the contrast enhancing species or the metabolites thereof, the design of liposomal agents with readily characterized metabolites whose biodistribution and bioelimination can also readily be investigated is simpler and more straight-forward than the design of macromolecular agent.

The chelating agent in the liposomal agent of the invention is thus a bifunctional species, having a chelating moiety and a membrane anchoring moiety attached thereto via a bond or a linker moiety. Advantageously, the linker moiety will incorporate a biodegradable linkage so that low molecular weight chelate molecules may be released from the liposomes, either before or after liposome degradation occurs, so as to facilitate their bioelimination. For this purpose it is especially preferred that the chelate moiety, optionally together with its post degradation residue of the linker moiety, is water-soluble.

Such anchor—biodegradable linker—macrocyclic chelant compounds, their salts and chelate complexes, are themselves novel and form a further aspect of the invention.

Particularly preferably the linker moiety will at least in part arise from the reaction to couple a macrocyclic chelant to a lipophilic anchor molecule. Thus, while the lipophilic anchor-macrocyclic chelate may be prepared before liposome formation is effected, it is especially preferred that such compounds be prepared in situ by coupling a macrocyclic chelant, or more especially a metallated macrocyclic chelant, to a molecule which already is incorporated into the liposomal membrane.

Thus one especially preferred class of chelant molecules are those of the general formula I

An—L—Ch(R)$_n$      (I)

where An is a hydrophobic, membrane associating group, L is a linker moiety attached to a ring atom of Ch and severable at a biodegradable bond, and Ch is a macrocyclic chelant moiety optionally carrying one or more hydrophilic or site-directed groups R (ie. n is 0 or a positive integer).

In an alternative embodiment, the chelating agent is an amphiphilic compound as described in PCT/GB95/00833 (a copy of the text of which is filed herewith and the contents of which are incorporated herein by reference), i.e. a compound of formula II

(R)$_n$Ch—L'—Ar—(AH)$_q$      (II)

where (R)$_n$Ch is a hydrophilic macrocyclic chelant moiety as defined above, L' is an optionally oxo-substituted $C_{2-25}$ alkylene linker moiety attached to a ring atom of Ch and in which at least one $CH_2$ moiety is replaced by an oxa, aza or thia group and which is optionally interrupted by a biodegradable group M, Ar is an aryl ring optionally substituted by or having fused thereto a further aryl ring, q is a positive integer, preferably 1 or 2, and each AH is a protic acid group, e.g. a carbon, sulphur or phosphorus oxyacid.

The chelant moiety $Ch(R)_n$ is conveniently a group of formula

where p is 3, 4, 5 or 6, preferably 4;
each m is 2, 3 or 4, preferably 2;
each $R_1$ is a hydrogen atom, a hydrophilic group, or a site-directed group;
and each X is a group $R_1$ or a metal coordinating group, with however one carbon or nitrogen attached $R_1$ group providing a bond to the linker moiety.

Examples of preferred coordinating groups include $C_{1-3}$ linear alkyl groups substituted by carboxyl, phosphonate or sulphonate groups, and optionally further substituted by one or more $R_1$ groups. Particularly preferred are carboxymethyl and phosphonomethyl groups.

Examples of preferred hydrophilic groups include hydroxylated and/or alkoxylated alkyl groups, eg. hydroxymethyl, 2-hydroxyethyl, 3-hydroxypropyl, 2,3-dihydroxy-propyl, and 2-hydroxyethoxyethyl groups.

In the chelating and linker moieties referred to herein, unless otherwise specified alkyl and alkylene moieties preferably contain 1–6 carbon atoms.

Thus preferred chelant moieties include groups of formula

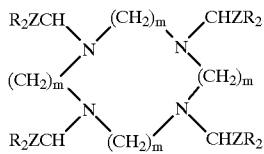

(where each m is 2, 3 or 4, preferably 2;
each $R_2$ is hydrogen or an alkyl group substituted by at least one hydroxy, alkoxy, amino, oxo, carboxyl, sulphonic acid, bromoacyl, isothiocyanate or site-directed group and optionally substituted by or incorporating a homo or heterocyclic saturated or unsaturated ring; and
each Z is a $CO_2H$, $PO_3H$, $CON(R_2)_2$ or $R_2$ group, at least 2 and preferably all 3 being COOH or $PO_3H$ groups; and
one $R_2$ group being a bond to the linker moiety).

Especially preferred chelant groups include DO3A and DOTA residues, eg.

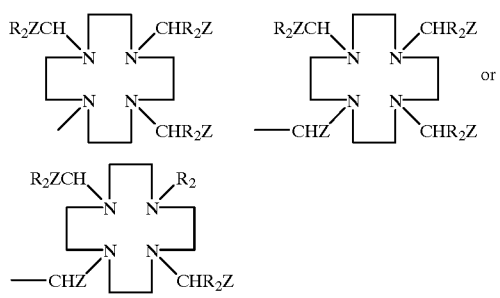

(where each Z is COOH or $PO_3H$, preferably COOH and each $R_2$ is hydrogen or a hydrophilic group, eg. a $C_{1-4}$ mono or polyhydroxy alkyl group).

Particularly preferably the chelant residues are simple DO3A residues of formula

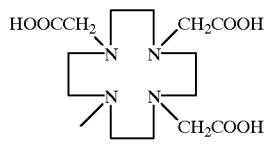

and DO3A monoamides such as described in WO 95/24225 and PCT/GB95/00833.

The hydrophobic "anchor" group used to tether the chelant moiety to the liposomal membrane may be any hydrophobic group which can serve this function.

Generally it will comprise one or more, eg. 1, 2, 3 or 4 but preferably 1 or 2, lipophilic chains, or mono or polycyclic saturated or unsaturated groups, the latter optionally being substituted by branched or linear, optionally unsaturated $C_{1-12}$ alkyl groups, fluorine atoms or carbon, sulphur or phosphorus oxyacid groups or esters or amides thereof, eg. $C_{1-20}$ alkyl esters or alkylamides in which the alkyl groups are optionally unsaturated or fluorinated. Single chain anchor groups in the chelating agents of formula II above may, when in situ in the liposome, be folded to present the $(R)_nCh$ and $Ar(AH)_q$ groups on the membrane surface with the folded linker $L'$ acting as the membrane associating anchor.

Examples of suitable cyclic groups include phenyl, biphenyl, naphthyl, 5–7 membered O, N or S containing heteroaryl groups, steroid groups, etc. Examples of suitable hydrophobic linear groups include $C_{12-18}$ saturated, unsaturated or fluorinated, eg. perfluorinated alkyl groups.

Many suitable anchoring groups are known from the literature. See for example Kinsky in Biochim Biophys Acta 769: 543 (1984), Kung in Biochim Biophys Acta 862: 435 (1986), Gregoriades in Biochem Soc. Trans. 17: 128 (1989), Wessig in Biochim Biophys Acta 1003: 54 (1989), Dancy in J. Immunol 122: 638 (1979), Carroll in J. Med. Chem 29: 1821 (1986), Unger in WO92/21017 and Herslöf in WO92/21384.

Preferred examples of phospholipids which can be used as anchoring groups in this way include $C_{4-14}$ α, ω-alkane-dicarboxylic acid amides of phosphatidylethanolamines (PE) e.g. dioleoyl, dipalmitoyl or other two fatty acid chain carrying PE's (such as N-succinyl, N-glutamyl and N-dodecenyl-PE) and amides of cholesterol.

In a preferred embodiment of the invention, the anchor group is coupled to the chelate moiety after liposome formation has been effected. For this purpose, anchor compounds which incorporate into the liposome membrane leaving a functional group (for direct or indirect chelate attachment) on the membrane's exterior are used.

Such compounds conveniently include a spacer moiety, which especially conveniently is of amphiphilic nature, between the anchor group and the chelate attachment group. Examples of such compound include the compounds of formulae II to V below

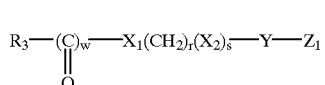 (II)

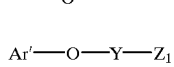 (III)

-continued

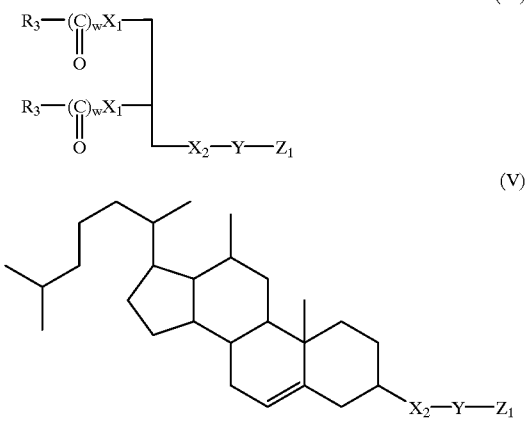

(where each $R_3$ independently is a $C_{12-}$ saturated, unsaturated or perfluorinated alkyl group;
w is 0 or 1;
each $X_1$ independently is a bond, an oxygen or sulphur atom or an NH group;
r is 0, 1, 2, or 3;
s is 0 or 1;
$X_2$ is a bond, an oxygen or sulphur atom or an NH or —$OPO_3H$— group;
Y is a $(CH_2)_r$, $(CH_2CH_2O)_r$, $(CH_2)_t$ $X_1$—Ar'—$X_1(CH_2)_t$ or $(NHCH_2CO)_t$ group;
each t is an integer of 0 to 12;
each Ar' is a phenyl, biphenyl, naphthyl or 5 to 7 membered O, N or S containing heteroaryl group, optionally substituted by COOH, $SO_3H$, $PO_3H$, $PO_2H$ or $COOR_3$ groups;
$Z_1$ is a $CO_2H$, $NH_2$, COO-succinimide, maleimide, thiol, $COCH_2R_4$, Ar' NCS, Ar' $N_3$, Ar' NCO or CHO group; and
$R_4$ is a OTs, OMs, I, Br or Cl group).

The linker group in the anchor:chelate conjugates may be any group which serves to connect the hydrophobic anchor group (or groups), which buries into the liposome membrane, with the chelate group which is outside the membrane. Depending on the mode of manufacture of the chelate carrying liposome, the linker may or may not contain groups which are the result of anchor compound chelate compound conjugation; however this will generally be the case. Similarly, they may or may not, but preferably will, include hydrophilic, or more preferably amphiphilic, sections which will serve to space the chelate group away from the membrane surface. Moreover the linker group will preferably include a biodegradable function which is severable to release chelate molecules (the term molecule as used herein includes charged and uncharged species) to facilitate their bioelimination or, perhaps in the case of therapy, to facilitate release of the therapeutic metal at the site of interest.

Examples of suitable biodegradable functions include ester, carbamate, double ester and disulphide bonds. Double ester bonds, ie. bonds of formula —O—CO—O—$CH_2$—O—CO—O— from which one or both of the terminal oxygens may be omitted and in which the methylene group may be substituted, are particularly suitable as biodegradable bonds.

Thus the linker moiety conveniently comprises a linear or branched $C_{2-20}$ alkylene chain, optionally terminated or interupted by N, O, S and P atoms or by homo or heterocyclic saturated or unsaturated rings and optionally substituted by oxygen or fluorine atoms or by hydroxy, amine, alkoxy, imino, alkyl or aryl groups, the alkoxy, imino, alkyl or aryl groups themselves optionally being substituted by hydroxy, amine or $C_{1-5}$ alkoxy groups.

Where the linker groups are attached to ring heteroatoms of the anchor or chelate moieties, the terminal atom of the linker will generally be carbon. For DO3A and DOTA-like $N_4C_{12}$ macrocycles, attachment is preferably via a ring nitrogen, eg. via the residue of a N-carboxymethyl group or of a ring NH group, although, albeit less preferably, attachment can be at a ring carbon, eg. using C- aralkyl-substituted chelates such as those proposed by Meares et al. (see Bioconjugate Chem. 3: 563 (1992)) for the anchor:chelate coupling reaction.

The chelate molecule, for such coupling reactions then preferably carries a reactive side chain (preferably attached at a ring nitrogen) which carries a reactive group such as a carboxyl, thiol, NCS or amine group. The chain on which this is carried is conveniently a $C_{1-20}$ alkylene group optionally interupted by an aryl group or by N, O or S atoms and optionally substituted by oxo, alkyl or fluorine, eg. a —$CONHCH_2CH_2NH_2$, $CONHCH_2CH_2NHCO(CH_2)_3$ COOH. Groups such as these can readily be formed at a DOTA or DO3A N-carboxymethyl or —NH—site.

For the chelating agents of formula II above, examples of preferred linker structures L' include $(CH_2)_dO$ where d is 1 to 15 where Ar is bicyclic and 6 to 15 where Ar is monocyclic, and preferred Ar(AH)$_q$ groups include 4-carboxyphenyl and 3,5-bis carboxyphenyl. Particularly preferred chelating agents of formula II include the following

| Name | $(R)_nCh$ | L' | Ar(AH)$_q$ |
| --- | --- | --- | --- |
| DO3A DOBA | DO3A | $(CH_2)_{10}$ O* | 4-carboxyphenyl |
| DO3A DOIA | DO3A | $(CH_2)_{10}$ O* | 3,5biscarboxyphenyl |
| DO3A DOmBA | DO3A | $(CH_2)_{10}$ O* | 3-carboxyphenyl |
| DO3A OOBA | DO3A | $(CH_2)_8$ O* | 4-carboxyphenyl |
| DO3A HOBA | DO3A | $(CH_2)_6$ O* | 4-carboxyphenyl |
| DO3A DOoBA | DO3A | $(CH_2)_{10}$ O* | 2-carboxyphenyl |

*oxygen attached to Ar

The selection of metals to be chelated by the chelant moiety will of course depend upon the desired end use of the liposomal agents of the invention, but will generally be from paramagnetic, heavy or radioactive metal alone or in polyatomic clusters.

The liposomal agents will generally include, besides the anchor:chelate molecules, liposome membrane forming compounds, ie. lipids and in particular phospholipids, as well as the materials which make up the liposome core and its external environment, generally in each case an aqueous medium.

The liposomes themselves are spherical vesicles having a lipid layer surrounding a central space. The present invention is particularly concerned with unilammellar and multilamellar liposomes which respectively have a single lipid bilayer or multiple lipid bilayers surrounding an aqueous core.

Liposomes spontaneously form upon dispersion of lipids, particularly phospholipids, in aqueous media and the liposomal structure of the agents of the invention can be produced by conventional techniques. Such conventional techniques are referred to in WO92/21017 (Unger) and by Papahadjopolous in Ann Rep. Med. Chem. 14: 250–260

(1979) and include reverse evaporation, freeze-thaw, detergent dialysis, homogenization, sonication, microemulsification and spontaneous formation upon hydration of a dry lipid film. Multi-lamellar liposomes can be used according to the invention or may be converted to liposomes with lower lamellarity, or to unilamellar liposomes, by known methods. Unilamellar liposomes can also be prepared directly.

Liposome preparations are typically heterogeneous in size and the liposomes used according to the invention may be sized to the desired diameter by known techniques, eg. extrusion, freeze-thaw, mechanical fragmentation, homogenization and sonication. The liposomes used according to the invention are advantageously 20–5000 nm diameter, unilamellar or multi-lamellar.

The liposomes may be lyophilized to increase shelf life and lyophilized liposomes may be reconstituted by vigorous shaking with aqueous buffer prior to use. Formulations may include agents which serve to stabilize the liposomal material for the lyophilization procedure.

Liposomes smaller than 200 nm may be sterilized after formulation by filtration through a 0.2 μm filter.

The lipids used as the liposomal membrane forming molecules are typically phospholipids or hydrogenated phospholipids such as natural or synthetic phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides or cerebrosides, eg. liposome membrane forming compounds such as are described in WO-92/21017.

The membrane forming lipids may also comprise polymerizable lipids, eg. methacrylate lipids, thiol and disulphide lipids, dienoate lipids, styryl lipids and diacetylanic lipids as described by Johnston in Liposome Technology Vol. I, Gregoriades Ed., pages 123–129 (1983) and Singh in Phospholipid Handbook, Cevc Ed., Dekker, pages 233–291 (1993) and references therein. The use of polymerizable lipids in the formation of the liposomes provides one route for increasing liposome stability.

The liposomal membrane can also have steroids and other compounds incorporated into it, eg. to affect the biodistribution of the liposome. Suitable steroids include for example cholesterol, cholesterol derivatives, cholestane, cholic acid, and bile acids, but particularly cholesterol.

The inclusion of steroids serves to modify the fluidity of the liposome membrane and this affects biodistribution. Thus higher transition temperature lipids lead to longer blood half lives and the inclusion of cholesterol results in a more rigid and less permeable bilayer. A decrease in RES-uptake is observed with the addition of cholesterol.

The biodistribution modifiers can be incorporated by the use of a phospholipid derivative having a pendant biodistribution modifying function, by the use of a biodistribution modifying agent having a hydrophobic "anchor" moiety which associates with the liposomal membrane or by coupling a biodistribution modifier to an anchor molecule (such as discussed above in relation to chelate tethering) present in the liposomal membrane.

Particularly preferred biodistribution modifers include compounds, especially amphiphilic polymers, which serve to reduce in vivo protein binding to the liposome and thus prolong the half life of the liposomes in the blood. Polyalkyleneoxy polymers, such as polethylene glycol (PEG) and gangliosides, such as $Gm_1$, are effective in this regard.

Incorporation of 1–10%, relative to the weight of liposome membrane forming material, of PEG-PE derivatives significantly thus extends blood half life.

Liposomes prepared from perfluorinated phospholipids (see Santaella, FEBS Letters 336: 481–484 (1993) and Angew, Chem. Int. Ed. Eng. 30: 567–568 (1991)) can also extend blood half-lives.

Active targetting to specific organs or tissues can be achieved by incorporation of lipids with attached thereto monoclonal antibodies or antibody fragments that are specific for tumor associated antigens, lectins or peptides.

Liposome biodistribution is also significantly dependent upon surface charge and the liposomes according to the invention may desirably include 1 to 10%, relative to the weight of liposome membrane forming material, of negatively charged phospholipids such as for example phosphatidylserine, phosphatidylglycerols, phosphatidic acids, and phosphatidylinositol.

As discussed above, the chelated metals can be tethered to the liposomes in several ways, for example:

(i) by metallation of chelant groups tethered to the surface of preformed liposomes;

(ii) by coupling chelate moieties to anchor molecules in preformed liposomes;

(iii) by forming liposomes using a lipid mixture including chelate:anchor molecules.

All three methods represent aspects of the present invention. These processes simplify the procedure for preparing membrane bound agents by avoiding the synthesis and purification of hydrophobic chelates (implicit in process (iii)) and by avoiding the unwanted weak (easily reversible in vivo) binding of metal to liposome that is associated with process (i).

As mentioned, the liposomes of the invention preferably are produced by coupling metallated chelate molecules to anchor molecules in pre-prepared liposomes. In this way the chelate is only bound to the exterior of the liposome membrane. Liposomes which are formed with derivatized chelates have the complex attached to both the interior and exterior of the membrane. The water permeability of the membrane or rate of diffusion of the bulk water through the membrane will determine the relaxivity of the inner paramagnetic ions. With tight, stable liposomes, the relaxivity of gadolinium inside the liposome may be very low. Thus with the chelate groups tethered only to the liposome exterior the efficiency of usage of the metal is optimized, ie. the liposomes have a high relaxivity per metal ion.

Having the chelates linked only to the exterior of the liposomes is also an advantage for binding radionuclides, especially α-emitters, since the membrane of the liposome does not have to be penetrated by the alpha rays.

Thus the liposomes may be prepared by a conventional method from a phospholipid mixture which includes the anchor compound, a compound having a hydrophobic anchor moiety tethered to a reactive functional group which provides an attachment point for the chelate moiety. The liposomes can then be sized to the required diameter by known methods. The reactive functional group is then coupled to a compatible functional group on the chelate and the unreacted low molecular weight agent can readily be removed, eg. by gel permeation chromatography, dialysis or ultrafiltration.

The anchor compound conveniently comprises 5–50% relative to the total weight of the liposome membrane forming compounds, preferably 10–30%. The coupling efficiency, of the chelate to the externally directed reactive groups that is, can be very high indeed, eg. about 90%.

The reactive groups on the anchor compound may simply be primary amines on a liposome membrane lipid which can be reacted with non-coordinating carboxyl group of a chelate molecule. In general most known methods of coupling chelates to macromolecules, such as proteins, may be used for chelate attachment to liposomes. The surface chemistry will however be limited by liposome stability and thus monitoring the pH and osmolality of the reaction mixture may be desirable. A few examples of coupling strategies are illustrated schematically below:

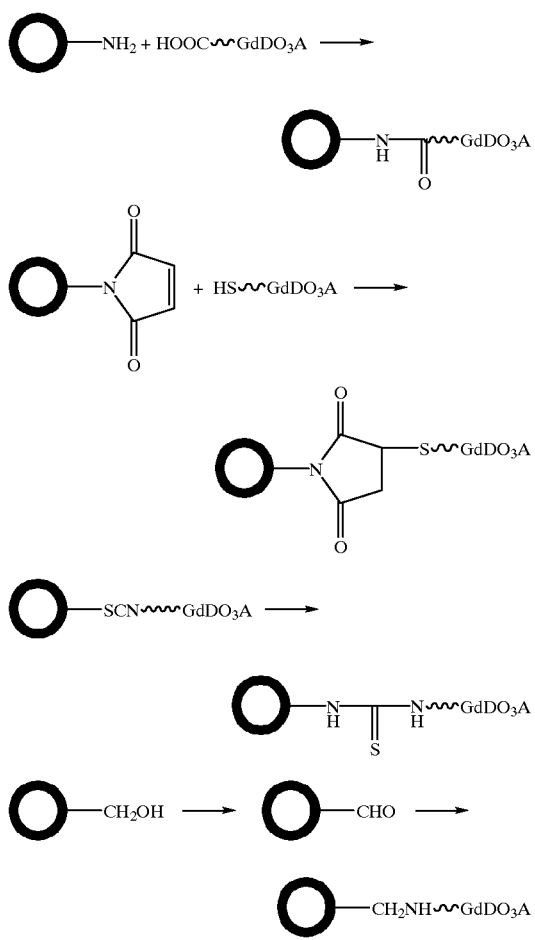

As an alternative to coupling chelates to anchor groups in the liposome, the anchor groups can be coupled to the chelate prior to liposome formation. The chelant is metallated in aqueous solution and then the chelate is coupled to the anchor molecule by conventional methods using a mixed solvent. The liposome is then formed using a lipid mixture including the chelate:anchor molecules. This avoids difficulties with non-specific binding of metal ions to liposomes which can occur when chelates are metallated In itu on the liposome surface as well as solubility problems associated with metallating water-insoluble chelants prior to liposome formation. The metal ions also serve as protecting groups during liposome formation for potentially active chelant groups.

To produce the contrast media compositions of the invention, the liposomes are formulated in physiologically tolerable liquid carrier medium, eg. an aqueous solution which may include one or more additives, such as pH modifying agents, chelating agents, antioxidants, tonicity modifying agents, cryoprotectants, further contrast agents, etc.

Examples of suitable ingredients to adjust the pH, include physiologically tolerable acids, bases and buffers, such as acetic acid, citric acid, fumaric acid, hydrochloric acid, malic acid, phosphoric acid, sulfuric acid, or tartaric acid, ammonia, ammonium carbonate, diethanolamine, diisopropanolamine, potassium hydroxide, sodium bicarbonate, sodium borate, sodium carbonate, sodium hydroxide, trolamine, ammonium phosphate, boric acid, citric acid, lactic acid, potassium metaphosphate, potassium phosphate monobasic, sodium acetate, sodium biphosphate, sodium citrate, sodium lactate, sodium phosphate, Tris, and N-methyl glucamine.

Examples of suitable chelating agents include EDTA, DTPA, DTPA-BMA and salts and complexes thereof especially calcium, sodium or meglumine salts, eg. edetate disodium, edetic acid, calcium EDTA.

Examples of suitable anti-oxidants include ascorbic acid, ascorbyl palmitate, cysteine, monothioglycerol, butylated hydroxyanisole, butylated hydroxytoluene, hypophosphoric acid, propyl gallate, sodium bisulfate, sodium formaldehyde sulfoxylate, sodium metabisulfate, sodium thiosulfate, sulfur dioxide, or tocopherol.

Examples of suitable tonicity agents, include sodium chloride, glucose, sucrose, mannitol, sorbitol and dextrose. These agents preferably are used to make the formulation isotonic or near isotonic with blood.

Examples of suitable anti-microbial agents include, benzalkonium chloride, benzyl alcohol, chlorobutanol, metacresol, methyl p-hydroxybenzoate, propyl p-hydroxybenzoate, and timerosal.

Examples of suitable cryoprotectants, agents which aid in the lyophilization and reconstitution processes include sodium chloride, sorbitol, mannitol, glucose and polyethyleneglycol.

The liquid carrier may as mentioned contain a secondary contrast agent. This would result in the second agent being entrapped in the inner aqueous volume of the liposome. Agents in the exterior aqueous volume may or may not be removed. This can be done to prepare a dual contrast medium [eg. as described in WO 89/09625]. For example, a $T_2^*$ susceptability agent such as a soluble dysprosium complex such as DyDTPA-BMA could be entrapped within a liposome with a $T_1$ relaxation agent, eg. a gadolinium complex such as GdDO3A being attached to the outside of the membrane. Secondary agents include for example water soluble MRI, X-ray, scintigraphic, and light imaging agents.

Other examples of further contrast agents which may be enclosed within the liposomes include heavy metal clusters and their chelate complexes, as described for example in WO91/14460 and WO92/17215. Such liposomes may be used for example as X-ray contrast agents especially $(Ct)_2L_3$ clusters (where Ct is a metal cluster, e.g. a $W_3$ or $W_4$ cluster and L is a ligand).

The chelated metal in the liposomal contrast agents of the invention will be selected to provide contrast in the imaging modality of choice. For MRI and magnetometric imaging, this will generally involve chelation of relaxation time (ie. $T_1$, $T_2$ or $T_2^*$) modifying centres, such as paramagnetic metal ions, and polyatomic cluster ions.

For X-ray imaging and CT imaging, the chelated metal species will generally be high atomic number (and hence high X-ray cross section) metal ions with atomic numbers of 37 or above, or polyatomic cluster ions.

For light imaging, the metal chelate moiety will be a chromophore or fluorophore having a characteristic absorption or emission peak. For SPECT, PET and scintigraphy an appropriate metal ion radioemitter is chelated.

Thus, in the field of MRI, the invention covers in particular liposomal contrast agents that incorporate multiple complexes of contrast enhancing species which are attached to the bilayer of the liposomal membrane. The contrast enhancing species may be any magnetic metal ion, metal ion cluster, or microcrystal. This includes in particular ions and cluster ions with the atomic numbers 21–29, 42, 44, or 57–71. Positive MRI agents may typically include metal ions Eu (III), Gd (III), Dy (III), Ho (III), Cr (III), Fe (III), or Mn (II). Negative contrast agents typically include Tb (III), Sm (III) and especially Dy (III) ions.

Attachment of radioisotopes to the liposomes is useful for scintigraphic imaging or as therapeutic agents. Particularly preferred are the following radioisotopes: $^{99m}TC$, $^{51}Cr$, $^{201}Tl$, $^{67}Ga$, $^{68}Ga$, $^{111}In$, $^{168}yb$, $^{140}La$, $^{90}Y$, $^{88}y$, $^{153}Sm$, $^{156}Ho$, $^{165}Dy$, $^{64}cu$, $^{97}Ru$, $^{103}Ru$, $^{186}Re$, $^{188}Re$, $^{203}pb$, $^{211}Bi$ $^{212}Bi$, $^{213}Bi$, $^{214}Bi$. The choice of metal ion will be determined based on the desired therapeutic or diagnostic application.

For X-ray, non-radioactive heavy metal ions will generally be chelated. This invention includes the use of metal ions with atomic number greater than 37 and, in particular, metal ions with atomic numbers greater than 50. Particularly preferred are multinuclear clusters as described in WO91/14460.

For use as light imaging agents, the contrast agents of the invention should preferably include an absorbance or fluorescence moiety having an absorbance or emission in the near IR (670–1300 nm), preferably red-shifted toward 1300 nm. The extinction coefficient should be as large as possible, preferably greater than or equal to $10^5$ cm$^{-1}$M$^{-1}$.

For the liposomal contrast agents of the invention to be echogenic, ie. capable of functioning as ultrasound contrast agents, it is preferred that they have a di or oligolamellar structure with a separation between the lamellae. Lipids containing a tether with an ionizable group (such as carboxylate) should have a relatively large distance between the concentric phospholipid bilayers. This should increase the acoustic reflection of the liposomes. This invention includes the incorporation of derivatives of lipids for this purpose.

Alternately, perfluorinated lipids could be used as components of the liposomes. As well as increasing the blood resonance time of the liposomes, using perfluorinated lipids may enhance the acoustic properties of the liposomes.

As discussed above, possible hydrophobic anchors, ie. the membrane-associating moiety in the contrast enhancing species, may include phospholipids, long alkyl chain or a molecules containing multiple long alkyl chains including esters and amides of fatty acids, steroid, aromatic and polyaromatic groups. The anchoring group may be designed to enhance the elimination of the contrast enhancing moiety (eg. chelate complex) once deposited in the liver. The elimination may be controlled by balancing the hydrophobic and hydrophilic nature of the overall molecule eg. by including potentially ionizable groups such as carboxylic, phosphonic, or sulfonic acids in the contrast enhancing moeity. In this way it could be possible to mimic the structure of biologically relevant compounds that are rapidly excreted from the liver. Alternately, the hydrophobic anchor could contain a polymerizable group, enabling formation of a more stable liposome by polymerization of the hydrophobic anchor with the bulk lipid of the vesicle.

The linkage between the contrast enhancing moiety and the membrane associating moiety in the contrast enhancing species may be relatively inert to biodegration (such as an alkyl, aryl, or ether group) or may be hydrolyzable, eg. including a carboxylic or carbonic ester, disulfide, acetal, ketal, thioester, carbamate, amide, lactam, thiourea, or urea group. The linking moiety may include a spacer to act as a tether, such as a saturated and unsaturated alkyl chain and/or ring structures such as alicyclic, aromatic, polyaromatic, and heterocyclic groups. The length and flexibility of the spacer may be altered to optimize the coupling efficiency and relaxivity of the agent. The linker may be hydrophobic, so that it is buried in the lipid bilayer or hydrophilic, so that it extends into the aqueous media. The linking group may thus play an important role in controlling the metabolic and elimination pathways of the contrast enhancing moiety.

The composition and size of the liposome can be selected so as to control the biodistribution of the agent. For example, liposomes with positive or negative surface charge can be prepared by incorporation of lipids with charged polar head groups. When intravenously administered, the surface charge affects the biodistribution of the agents [see Paphadjopolous, in Biochim. Biophys. Acta. 1103: 185–197 (1992)]—negatively charged liposomes are taken up more rapidly by the RES than neutral or positively charged liposome, while positively and negatively charged liposomes accumulate in the lungs to a greater extent than neutral liposomes.

Additionally, the diameter of the liposomes affects their biodistribution and pharmacokinetics. Small liposomes have a longer circulation times than large liposomes. Kupffer cell uptake is faster with large liposomes, whereas hepatocytes take up small liposomes at a faster rate. Very large liposomes (>100 $\mu$m) are trapped in the lungs after injection.

The hydrophilicity of the lipid membrane also affects the circulation time of liposomes. Conjugation of hydrophilic or amphiphilic polymers such as polyethyleneglycol to the membrane surface increases circulation time up to 8000% by reducing the rate of phagocytosis by macrophages.

Active targeting with liposomes can be accomplished by attachment of ligands, carbohydrates, antigens, proteins, amino acids, oligopeptides, enzymes, hormones, antibodies, and antibody fragments to the exterior surface of the liposomes. Upon recognition of a receptor sites, the liposomes bind to the target cells [see Jones, Adv. Drug Deliv. 13 : 215–250 (1994), U.S. Pat. No. 4,603,044, J. Med. Chem., 29: 1821–1826 (1986), Ann. N.Y. Acad. Sci., 698: 427–43 (1993), Liposomes Technology, Gregoriadis, ed. vol. II, (1983), and references therein]. This invention also provides for the attachment of multiple site directing targeting agents to the exterior surface of the liposome, preferably relatively low molecular weight moieties such as peptide or antibody fragments.

The contrast agents of the invention may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.001 to 1.2, e.g. 0.01 to 0.5, mmoles/kg bodyweight while for X-ray applications dosages of from 0.5 to 1.5 mmoles/kg are generally effective to achieve X-ray attenuation. Preferred dosages for most X-ray applications are from 0.8 to 1.2 mmoles of the lanthanide or heavy metal/kg bodyweight.

For X-ray applications, to extend the photon energy range over which the contrast agents of the invention are optimally effective two or more chelated metals may be used as mixtures of homopolychelates or as a heteropolychelate.

The liposomal agents of the invention provide several improvements over the prior art.

The rate of metal exchange is very important for blood pool imaging where the blood residence times are much longer than for ECF agents and for liver imaging where the chelate will be taken intracellularly and exposed to the acid environment of the lysosomes. The use according to the invention of macrocyclic chelant groups is important because of the increased complex stability. Moreover the chelate moieties, such as D03A-Gd(III), can be neutral or of selected charge and this can be an advantage in controlling the biodistribution, since the surface charge of the liposome determines its fate in vivo.

With attachment of premetallated chelates to preformed liposomes according to the preferred manner of manufacture of the liposomes of the invention, unbound chelate can be easily removed form the liposome and recycled and since the metal ion is already bound to the chelate this prevents non-specific binding of metal ions to the liposome or conjugated targeting agents.

The contrast agent of the invention allows particularly effective elimination of the chelated metal. The prior art has not satisfied this requirement. The elimination of radioactive chelates in mice for encapsulated and membrane bound agents was studied. Example 13 hereof has a better elimination half-life than an encapsulated GdD03A complex (3.2 vs. 6 days).

A further aspect of this invention is that using a biodegradable linkage results in a mechanism for time release of the chelated species. This is especially useful for therapeutic agents, ie. agents where the chelated metal has a therapeutic function. Such therapeutic rather than diagnostic or contrast agents also form part of the invention.

All publications referred to herein are hereby incorporated by reference.

The invention will now be described further with reference to the following non-limiting Examples:

In the Examples gadolinium concentrations were determined by digestion of liposomal samples followed by analysis by ICP. The lipid concentrations were determined by digestion of the sample followed by spectrophotometric determination of phosphate concentration using molybdate. The liposomes were extruded using a Lipex extruder with two layers of the appropriate Poretics polycarbonate membranes. The size distribution of the liposomes were determined by laser light scattering using a Malvern Zetasizer 4.

The phospholipids used were obtained from Avanti Polar lipids. They were stored in a freezer under argon. Cholesterol was obtained from Aldrich and cholsterol hemisuccinate from Sigma. 1-(3-Dimethylaminopropyl)-3-ethylcarbodiimide hydrochloride (EDAC) was obtained from Aldrich and stored in a freezer. Dipalmityl PE-glutaryl was prepared by the method of Torchilin [see Phospholipid Handbook, Marcel Dekker, Inc., G. Cevc, ed., chapter 8], 6-(cholesteryl)-7-oxaheptan-1-ol was prepared by the method of Carroll [see J. Med. Chem., 29, 1821, 1986], and cholesterol-O-tosylate was prepared by the method of Koswer [see JACS, 78, 4347–4355 (1956)].

EXAMPLE 1

1,4,7-Tri-tertbutoxycarbonylmethyl-10-methoxycarbonyl-methyl -1,4,7 10-tetraazacyclododecane 1,4,7-Tri-tertbutoxycarbonylmethyl-1,4,7,10-tetraazacyclo-dodecane hydrobromide (25.0 g, 42 mmol) was slurried in acetonitrile and treated with TMG (70 mL). Methyl bromoacetate (6.5 g, 42 mmol) was added in one portion, and the mixture was refluxed for 3 hours. After stirring at ambient temperature for an additional 18 hours, the solvent and excess TMG were removed by rotary evaporation. The residue was dissolved in $CHCl_3$, washed with water, and dried ($Na_2SO_4$). Evaporation of the solvent afforded the title product as a pale oil (23 g, 95%). $^1$H NMR ($CDCl_3$) 1.4 (s, 27 H), 2.8 (s, 16 H), 3.2 (s, 6 H), 3.4 (s, 2 H), 3.6 (s, 3 H).

EXAMPLE 2

1,4,7-Tri-tertbutoxycarbonylmethyl-10-(N-(2-aminoethyl)-amido-methyl-1,4,7,10-tetraazacyclododecane The methyl ester of Example 1 (23.0 g, 40 mmol) was dissolved in methanol (500 mL) and treated with ethylenediamine (200 mL). The mixture was stirred at ambient temperature for 3 days. The solvent and excess ethylenediamine were removed by rotary evaporation, and the residue was dissolved in chloroform, washed with water, and dried ($Na_2SO_4$). The solvent was evaporated to yield the title product as a viscous oil (18 g, 75%). $^1$H NMR ($CDCl_3$) δ1.4 (s, 27 H), 2.5–3.0 (m, 20 H), 3.3 (m, 8 H), 6.0 (br s, 1 H).

EXAMPLE 3

1,4,7-Tri(carboxymethyl)-10-(N-(2-aminoethyl)amidomethyl)-1,4,7,10-tetraazacyclododecane [AE-D03A]

The ester of Example 2 (10.0 g, 16 mmol) was deprotected by reaction with neat TFA (200 mL) at ambient temperature for 3 hours. After removal of the TFA, the residue was dissolved in 1 M NaOH and loaded on an ion exchange column [AG 1×8 (OH—), 200 mL]. The column was washed with water and the product was eluted with 1.5 M HOAc. Concentration of the fractions containing the title product yielded 7.0 g (93%) as a white solid. $^1$H NMR ($D_2O$) δ2.9–3.6 (br mult.) Anal. Calcd. for $C_{18}H_{34}N_6O_7$ HOAc:C, 47.14; H, 8.11; N, 16.49. Found: C, 47.40; H, 7.98; N, 16.48.

EXAMPLE 4

1,4,7-Tri(carboxymethyl)-10-(N-(2-aminoethyl)amidomethyl)-1,4,7,10-tetraazacyclododecane Gadolinium (III) [GdAE-D03A]

The compound of Example 3 (1.0 g, 2.38 mmole) was dissolved in water (37 mL). The pH was adjusted to 5 by the addition of 1 M NaOH. Gadolinium (III) acetate was added in small portions until a slight excess of metal (by xylenol orange) was present. During the addition the pH was maintained at 5–6. The reaction mixture was stirred overnight at ambient temperature. Ligand (50 mg) was added and stirring was continued until a negative xylenol orange test was obtained. The water was removed under vacuum. The residue was chromatographed on Sephadex G-10 to remove inorganic salts. The fractions were analyzed by MS (FAB): $MH^+$=602.

EXAMPLE 5

1,4,7-Tri(carboxymethyl)-10-(N-(2-aminoethyl)amidomethyl)-1,4,7,10-tetraazacyclododecane-N-hemisuccinamide The compound of Example 3 (6.1 g, 13.6 mmol) in pyridine (20 mL) was heated until dissolution was complete. Succinic anhydride (1.5 g, 15 mmole) was added, and the mixture was heated for 1 hour. The solution was cooled and acetone was added to precipitate the product. The white solid was washed thoroughly with acetone and dried under vacuum to afford 5.0 g of the title product (67%).

EXAMPLE 6

1,4,7-Tri(carboxymethyl)-10-(N-(2-aminoethyl)amidomethyl)-1,4,7,10-tetraazacyclododecane-N-hemisuccinamide Gadolinium (III)

(A) The compound of Example 5 (1.9 g, 3 mmole) was dissolved in water (30 mL). The pH was adjusted with 1 N NaOH to 5.0. Gadolinium (III) chloride (~1.4/10 mL) in water was added dropwise until a slight excess of metal remained for several hours. Additional gadolinium (50 mg) was added, and the reaction mixture was stirred until a negative xylenol orange test was obtained. The water was evaporated, and the residue was chased several times with ethanol. The title product was purified by revese phase ($C_{18}$) preparative HPLC with 2% methanol in water as the mobile phase.

(B) The title compound was also prepared by an alternate procedure: The compound of Example 3 (240 mg, 0.4 mmole) in DMSO (10 mL) was heated at 80° until dissolution was complete. Succinic anhydride (40 mg 0.4 mmole) was added and the mixture was heated for 6 hours. After cooling to ambient temperature, acetone was added to precipitate the title product. The white powder was washed with acetone and dried under vacuum. MS (FAB): $MH^{30}$ 683.2, $MNa^+$ 705.1.

EXAMPLE 7
13-Cholesteryl-3,6,9,12-tetraoxa-dodecan-1-ol

Cholesterol tosylate (2.0 g, 3.7 mmol) and tetraethyleneglycol (6.42 mL, 37 mmole) were dissolved in dioxane (100 mL) and heated at 70° C. for 6 hours. The solvent was evaporated, and the residue was dissolved in toluene and washed thoroughly with water. The organic layer was dried ($Na_2SO_4$), and concentrated to an oil. The crude material was purified by chromatography on a short column of silica with gradient elution of 0–20% methanol in chloroform to afford 1.0 g (49%) of the title product as a pale oil.

EXAMPLE 8
13-Cholesteryl-3,6,9,12-tetraoxa-dodecan-1-oic acid

The compound of Example 7 (0.5 g) in acetone (20 mL) was oxidized by the dropwise addition of Jones reagent until a slight excess was present. The reaction mixture was treated with isopropanol and was filtered through a plug of silica gel. The crude title product was pure by TLC and NMR.

EXAMPLE 9
GdDO3A-stearyl amide

The compound of Example 3 (100 mg, 1.6 mmole) was dissolved in DMSO (10 mL) and was treated with stearoyl chloride (51 mg, 1.6 mmole). The reaction mixture was heated at 60° for 2 hours, and stirred overnight at ambient temperature. Water was added (50 mL) and the product was extracted into choloroform (3×100 mL. The extracts were dried, and concentrated to afford the title product as a white solid. MS (FAB) 868.5 $MH^+$.

EXAMPLE 10
GdAE-D03A cholesterol carbamate

The compound of Example 3 (300 mg, 0.8 mmole) was dissolved in DMSO (20 mL) and treated with cholesterol chloroformate (225 mg, 0.5 mmole). The reaction mixture was heated at 80° for 5 hours. The mixture was allowed to stand at ambient temperature until colorless cyrstals were deposited. MS (FAB): MH+ 1014.5, $MNa^+$ 1036.5.

EXAMPLE 11
LaD03A-succinyl-PE

LaD03A-Succinamide (130 mg, 0.2 mmole) was dissolved in DMSO (3 mL). Dicyclohexylcarbodiimide (39 mg, 0.2 mmole) was added followed by N-hydroxysuccinimide (22 mg, 0.2 mmole). The reaction mixture was stirred at ambient temperature for 1 hour, and PE (130 mg, 0.2 mmole) in chloroform (20 mL) was added. After 6 hours, the reaction mixture was filtered, washed with water, dried, and evaporated to yield the title product. TLC (65 $CHCl_3$/25 MeOH/4 $H_2O$/1 formic acid) Rf=0.2. MS (FAB): $MH^+$ 1400.7, $MNa^+$ 1422.7.

EXAMPLE 12
GdAE-D03A-glutaryl-PE

Egg PE-glutaryl (100 mg, 0.11 mmole) in chloroform (5 mL) was treated with N-hydroxysuccinimide (25 mg, 0.21 mmole) and dicyclohexylcarbodiimide (50 mg, 20.25 mmole). The reaction mixture was stirred at ambient temperature overnight and filtered to remove the urea. The compound of Example 4 (100 mg, 0.16 mmole) in methanol (1 mL) and 1 mL triethylamine were added. The reaction was stirred at ambient temperature for 6 hours, and evaporated to dryness. The residue was dissolved in chloroform (10 mL) and placed in a dialysis sac. The reaction was dialysed against sodium acetate buffer (1 L, 50 mM, pH 5.5, 12 hours), Tris buffer (1 L, pH 8, 50 mM, 5 hours), and deionized water (1 L, 5 hours). A small amount of precipitate which had formed in the chloroform layer was dissolved by the addition of methanol. The solution was dried ($Na_2SO_4$) and evaporated to yield the title product as a white, waxy solid (150 mg, 89%). TLC (65 $CHCl_3$/25 MeOH/4 $H_2O$/1 formic acid) $R_f$=0.2. MS (FAB): $MNa^+$ 1459.

EXAMPLE 13

A mixture of Egg PC (52 $\mu$mole) and Egg PE-glutaryl (48 $\mu$mole) in chloroform was evaporated to a thin film under vacuum. The lipid mixture was dissolved in diethyl ether (3 mL) and treated with 23 mL buffer (25 mM MES, 100 mM NaCl). An emulsion was formed by sonication of the mixture. The ether was evaporated to form a gel. The gel was collapsed by vortexing and evaporation of the residual solvent. An additional 1 ML of buffer was added and evaporation was continued until all traces of solvent were removed. The liposomes were treated with GdAE-D03A (140 mg) and EDAC (130 mg) overnight at ambient temperature with rapid stirring. Unreacted reagents were removed by passing the product through a Sephadex G-75 column (1×8 in). The liposomes were extruded three times through two 100 nm membrane. Analysis of the final mixture gave [Gd]=1.14 mM, [P]=5.04 mM. Based on the P/Gd ratio, 47.1% of the PE-glutaryl was derivatized. Relaxivity (water, 20 MHz) $r_1$=18±2 $(mMsec)^{-1}$.

EXAMPLE 14

The same procedure described for the synthesis of Example 13 was used. Egg PC (20 $\mu$mole) and dioleoyl PE-succinyl (17 $\mu$mole). Analysis of the final mixture gave [Gd]=0.56 mM, [P]=3.8 mM. Based on the P/Gd ratio, 30% of the PE-glutaryl was derivatized. Relaxivity (water, 20 MHz) $r_1$=18 ±2 $(mMsec)^{-1}$.

EXAMPLE 15

The same procedure described for the synthesis of Example 13 was used. Egg PC (10 $\mu$mole) and dioleoyl PE-dodecanoyl (8 $\mu$mole) were used. The liposomes were extruded (3×200 nm, 3×50 nm). Analysis of the final mixture gave [Gd]=0.66 mM, [P]=3.49 mM. Based on the P/Gd ratio, 43% of the PE-glutaryl was derivatized. Relaxivity (water, 20 MHz) $r_1$=17 ±2 $(mMsec)^{-1}$.

EXAMPLE 16

The same method used to prepare Example 13 was used for a mixture of Egg PC (56 $\mu$mole) and Egg PE (53 $\mu$mole). The liposomes were treated with EDAC (100 mg) and GDAE-D03A-succinamide (80 mg) overnight at ambient temperature with rapid stirring. After removal of the unreacted reagent, the liposomes were extruded (3×200 nm and 3×50 nm). Analysis of the final mixture gave [Gd]=0.39 mM, [P]=5.87 mM. Based on the P/Gd ratio, 14% of the PE-glutaryl was derivatized. Relaxivity (water, 20 MHz) $r_1$=27 ±2 (mmsec)$^{-1}$.

EXAMPLE 17

Liposomes were prepared from Egg PC (13 μmole) and cholesterol hemisuccinate (16 μmole) by the same method used to prepare Example 13. The liposomes were treated with EDAC (25 mg) and GdAE-D03A (25 mg). After removal of the unreacted reagents, the liposomes were extruded (3×200 nm and 3×50 nm). Analysis of the final mixture gave [Gd]=0.26 mM, [P]=2.93 mM. Based on the P/Gd ratio, 7.2% of the PE-glutaryl was derivatized. Relaxivity (water, 20 MHz) $r_1$=21 ±2 (mMsec)$^{-1}$.

EXAMPLE 18

Liposomes were prepared from Egg PC (80 μmole) and 6-(cholesteryl) -7-oxaheptan-1-ol (80 μmole) by the method described for preparation of Example 13. The liposomes were treated with EDAC (70 mg) and GdAE-D03A (40 mg). After removal of the unreacted agents, the liposomes were extruded (3×200 nm and 3×50 nm). Analysis of the final mixture gave [Gd]=0.39 mM, [P]=3.34 mM. Based on the P/Gd ratio, 11% of the PE-glutaryl was derivatized. Relaxivity (water, 20 MHz) $R_1$=19 ±2 (mMsec)$^{-1}$.

EXAMPLE 19

Liposomes were prepared from Egg PC (68 μmole), Egg PE-glutaryl (55 μmole) and Brain PS (6 μmole) by the method described for preparation of Example 13. The liposomes were treated with GdAE-D03A (40 mg) and EDAC (75 mg). After removal of the unreacted reagents, the liposomes were extruded (3×200 nm and 3×100 nm). Analysis of the final mixture gave [Gd]=0.51 mM, [P]=4.15 mM. Based on the P/Gd ratio, 299 of the PE-glutaryl was derivatized. Relaxivity (water, 20 MHz) $R_1$=19 ±2 (mMsec)$^{-1}$.

EXAMPLE 20

Liposomes are prepared by the method described for the synthesis of Example 13 from cholesterol hemisebacate (130 μmole) and Egg PC (130 μmole). The liposomes are treated with GdAE-D03A (120 mg) and EDAC (120 mg). Unreacted reagents are removed by gel chromatography and the liposomes are extruded.

EXAMPLE 21

The compound of Example 10 (71 mg, 6 μmole) was added to dioleolyl PC (15 mg, 20 μmole) in chloroform. The solvent was evaporated under vacuum. The residue was dissolved in ether (1 mL). Water (1 mL) was added, and the mixture was sonicated until an emulsion was formed. The ether was slowly evaporated under vacuum. A thick gel formed. Additional water (1 mL) was added and the gel was vortexed until the gel collapsed to form vesicles. The product was extruded (3×200 nm, 3×50 nm).

EXAMPLE 22

The compound of Example 12 (25 mg, 17.4 μmole) and Egg PC (13.7, 18 μmole) were dissolved in chloroform (3 mL). The solution was evaporated to dryness under vacuum. The residue was dissolved in ether (3 mL) and filtered. MES buffer (3 mL) was added and the mixture was sonicated until an emulsion formed. The ether was removed by evaporation under vacuum with occasional vortexing.

EXAMPLE 23

The compound of Example 9 (50 μmole) and hydrogenated Egg PC (150 μmole) are dissolved in a mixture of chloroform (10 mL) and methanol (2 mL). The solvent is evaporated at 75°. The residual thin film is hydrated in MES buffer at 75° by shaking. After freeze-thawing four times, the liposomes are extruded (3×100 nm) at 75°.

EXAMPLE 24

Pharmacokinetics

A catheter was inserted into the jugular vein of a rat days prior to the study. A 300 μL sample of blood was drawn and placed in a tared tube containing heparin prior to injection of the sample. The test compound was injected at time zero. Blood samples (300 μL) were taken at intervals over a 24 hour time period. At 7 days the animal was sacrificed, and the liver spleen, and kidneys were removed. Blood and organ samples were digested with nitric acid and hydrogen peroxide and analyzed for gadolinium concentration (μg/g) by ICP.

| Product of Example | Dose μg Gd/ Kg | $t_{1/2}$ min. | 7 Day Organ Retention | | |
|---|---|---|---|---|---|
| | | | Liver % | Spleen % | Kidney % |
| 13 | 831 | 98 | 9.9 | 1.3 | 0.7 |
| 13 | 1190 | 111 | 7.4 | 0.6 | 0.6 |
| 19 | 1764 | 69 | 24.0 | 11.8 | 0.5 |
| 20 | 1310 | 58 | 34.8 | 8.9 | 0.8 |

EXAMPLE 25

Biodistribution (2-Aminoethyl)-D03A was labelled with $^{153}$Gd. The chelate was coupled to 1:1 Egg PC/Egg Glutaryl liposomes (100 nm) as in Example 13. The radiolabelled liposomes were injected in the tail veins of mice. Three mice were used for each time point. Samples of blood, liver, spleen, kidney and skin were counted at 1 d, 3 d, and 7 d. The percent injected dose retained in each organ was calculated and is presented below. The elimination half-life for the liver was 3.2 d.

| | Organ Retention (% Injected dose) | | |
|---|---|---|---|
| | 1 day | 3 day | 7 day |
| Blood | 0.60 | 0.54 | 0.51 |
| Liver | 18.22 | 9.91 | 4.88 |
| Spleen | 0.86 | 0.79 | 0.69 |
| Kidney | 1.03 | 0.74 | 0.64 |
| Skin | 1.68 | 1.19 | 0.80 |

EXAMPLE 26

Synthesis of GdDOTA-DOBA (i) Synthesis of methyl p-(10-bromodecyloxy)benzoate

A mixture of 1,10-dibromodecane (18.01 g, 60 mmol), methyl p-hydroxy benzoate (9.12 g, 60 mmol) and $K_2CO_3$ (8.28 g, 60 mmol) in acetone (90 mL) was stirred at reflux for 20 hours. The white solid was filtered off and washed with acetone. The filtrate and washings were combined and concentrated to a white solid from which the desired product was isolated by column chromatography on silica gel using hexane/chloroform solvent gradient for elution (10.8 g, 48.4%). $^1$H NMR (CDCl$_3$, δ): 7.95 (d), 6.88 (d), 3.98 (t), 3.85 (s), 3.39 (t), 1.80 (m), 1.52 (m), 1.42 (m) and 1.29 (m). FABMS: 371 (MH+).

(ii) Synthesis of methyl p-(10-N-phthalimidodecyloxy)-benzoate

A mixture of methyl p-(10-bromodecyloxy)benzoate (10.44 g, 28.12 mmol) and potassium phthalimide (5.47 g, 29.53 mmol) in anhydrous DMF (175 mL) was stirred at 60° C. for 14 hours under nitrogen. The solvent was removed under vacuum and the residue was dissolved in CHCl$_3$ and washed with water (4×5 mL). The aqueous washings were combined and back-extracted once with CHCl$_3$ (100 mL). The combined organic layers were dried with MgSO$_4$ and the solution was concentrated to yield the crude product which was purified by chromatography on silica gel using hexane/chloroform solvent gradient for elution (11.8 g, 96%). 1H NMR (CDCl$_3$, δ): 7.95 (d), 7.81 (m), 7.68 (m), 6.86 (d), 3.97(t), 3.85 (s), 3.64 (t), 1.76 (m), 1.65 (m), 1.54 (m), 1.42 (m), 1.29 (m). FABMS: 438 (MH+).

(iii) Synthesis of methyl p-(10-aminodecyloxy)benzoate

Methyl p-(10-N-phthalimidodecyloxy)benzoate (8.52 g, 19.48 mmol) was dissolved in methanol (75 mL) at 65C. Hydrazine monohydrate (1 mL, 20.62 mmol) was added and the solution refluxed under nitrogen for 22 hours. The solution was cooled to ambient temperature and the precipitate was filtered. The solution was concentrated and the residue was combined with the precipitate and treated with chloroform (500 mL). The solution was washed with water and the washings back extracted with chloroform (2×100 mL). The combined organic layer was dried over MgSO$_4$ and concentrated to yield the product (5.62 g, 97%). 1H NMR (CDCl$_3$, δ): 7.95 (d), 6.88 (d), 3.97 (t), 3.86 (s), 2.64 (t), 1.78 (m), 1.53 (m), 1.43 (m), 1.28 (m).

(iv) Synthesis of methyl-p-(10-chloroacetamidodecyloxy)-benzoate

The crude product from (iii) above (5.62 g, 18.84 mmol) and triethylamine (2.6 mL, 18.7 mmol) were dissolved in chloroform (90 mL) and cooled in an ice bath. A solution of chloroacetyl chloride (1.5 mL) in chloroform (40 mL) was added dropwise with stirring. After the completion of the addition, the solution was stirred in the ice bath for 15 minutes and warmed to ambient temperature and stirred for 20 hours. The solution was washed with water (4×80 mL). Drying (MgSO$_4$) and concentration yielded the product (6.71 g, 93%) which was used without further purification. $^1$H NMR (CDCl$_3$, δ): 7.95 (d), 6.87 (d), 6.54 s, br), 4.01 (d), 3.96 (t), 3.86 (s), 3.28 (q), 1.76 (m), 1.55 (m), 1.45 (m), 1.29 (m). $^{13}$C NMR (CDCl$_3$, δ): 130.71, 130.66, 121.52, 113.23, 75.37, 67.33, 50.95, 41.85, 39.04, 28.56, 28.53, 28.47, 28.43, 28.33, 28.25, 25.94, 25.11.

(v) Synthesis of 10-(p-methoxycarbonyl-phenyloxydecylcarbamoylmethyl)-1,4,7,10-tetraazacyclododecane-1,4,7-tri-t-butyl acetate DO3A-tri-t-butyl ester (9.31 g, 15.63 mmol) and triethylamine were dissolved in DMF (90 mL) and the chloroacetamide from (iv) above (6.0 g, 15.63 mmol) was added to the solution which was heated at 60° C. under nitrogen for 19 hours. The solvent was removed under vacuum and the residue taken up in chloroform (200 mL). The solution was washed with water (3×100 mL), dried over MgSO$_4$ and concentrated to yield the crude product (10.97 g) as an oil.

(DO3A=1,4,7-Triscarboxymethyl-1,4,7,10-tetraazacyclododecane).

EXAMPLES 27–31

Using the following reaction scheme, analogs of DO3A-D0BA (the compound of Example 26) were prepared

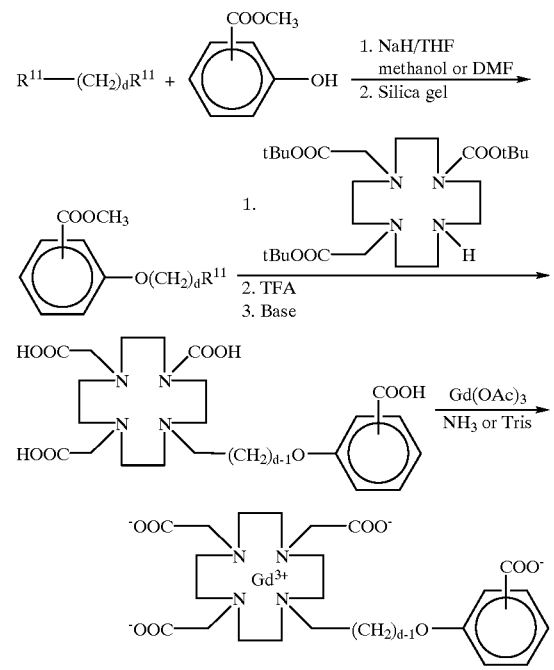

(where R$^{11}$ is halogen, eg. Br; X$^{11}$ is CH$_2$ or O; and d is a positive integer).

The synthesis of the compounds of Examples 27 to 31 was straightforward and reproducible in all cases.

| Example No. | -L'-Ar(AH)$_q$ | Short Name |
|---|---|---|
| 27 | m-carboxyphenoxy-(CH$_2$)$_{10}$ | DO3A-DOmBA |
| 28 | o-carboxyphenoxy-(CH$_2$)$_{10}$ | DO3A-DOoBA |
| 29 | 3,5-bis carboxy-phenoxy-(CH$_2$)$_{10}$ | DO3A-DOIA |
| 30 | p-carboxyphenoxy-(CH$_2$)$_6$ | DO3A-HOBA |
| 31 | p-carboxyphenoxy-(CH$_2$)$_8$ | DO3A-OOBA |

EXAMPLE 32

Liposomes Having Membrane-bound Gd DO3A-DOBA 110 nm sized liposomes were prepared using 90 mol % egg phosphatidyl-choline and 10 mol % Gd DO3A-DOBA in a 175 mM glucose, 100 mM sucrose medium of total osmolality 282 mOs T$_1$ relaxivity: 17 mM$^{-1}$s$^{-1}$ Gd concentration: 7.87 mM Lipid concentration: 65.9 mM Blood half life (rats) following iv injection at 0.03 mmol/kg: 20–90 min Tissue retention (as a percentage of injected dose):

| Time | Liver | Kidney | Spleen |
|---|---|---|---|
| 30 m | 53.22 | 1.87 | 0.74 |
| 1 h | 27.95 | 0.34 | 0.91 |
| 3 h | 7.31 | 0.26 | 0.85 |
| 1 d | 4.27 | 0.34 | 1.60 |
| 7 d | 1.85 | 0.36 | 0.61 |

Liposomes loaded with gadolinium chelates of the chelants of Examples 27 to 31 are prepared analagously.

EXAMPLE 33

Dual Contrast Agent 200 nm sized liposomes are prepared using Gd DO3A-DOBA as a membrane associating chelate, egg phosphatidylcholine as a membrane forming lipid and an aqueous glucose/sucrose solution as in Example 32. Dissolved Dy DTPA-BMA is incorporated within the liposomes at a Dy/Gd ratio of 2 to yield a dual contrast agent.

$T_1$ relativity=14.6 mM$^{-1}$s$^{-1}$ $T_2$* relativity=16.6 mM$^{-1}$s$^{-1}$

We claim:

1. A process for the preparation of a liposomal agent comprising liposomes having bound to a membrane thereof a chelated diagnostically or therapeutically effect metal ion, the chelating agent binding said metal ion having a macrocyclic chelant moiety with attached to a single ring atom thereof a lipophilic membrane associating moiety, said process comprising coupling an optionally metalated macrocyclic chelant compound to an anchor compound having a hydrophobic moiety incorporated within a liposomal membrane of a liposome and if required thereafter metalating said chelant compound.

2. A process as claimed in claim 1 wherein said chelating agent is an amphiphilic compound of formula II $$(HA)_q Ar\text{—}L'\text{—}Ch(R)_n \qquad (II)$$

where Ch is a macrocyclic chelant moiety optionally carrying one or more hydrophilic or site-directed groups R, and n is zero or a positive integer; L' is an optionally oxo-substituted $C_{2-25}$ alkylene linker moiety attached to a ring atom of Ch and in which at least one $CH_2$ moiety is replaced by an oxa, aza or thia group and which is optionally includes a biodegradable function Ar is an aryl ring optionally substituted by or having fused thereto a further aryl ring, q is a positive integer and each HA is a protic acid group.

3. A process as claimed in claim 1 wherein said chelating agent is of formula I $$An\text{—}L\text{—}Ch(R)_n \qquad (I)$$

where An is a hydrophobic membrane-associating group, L is a linker moiety attached to a ring atom of Ch and severable at a biodegradable bond, Ch is a macrocyclic chelant moiety optionally carrying one or more hydrophilic or site-directed groups R, and n is zero or a positive integer.

4. A process as claimed in claim 3 wherein in said chelating agent An comprises a cholesteryl or phosphatidyl group.

5. A process as claimed in claim 2 wherein in said chelating agent of formula II q is 1 or 2, Ar is phenyl and L' is a $C_6$ to $C_{15}$ alkyleneoxy group oxygen-attached to Ar.

6. A process as claimed in claim 1 wherein in said chelating agent $Ch(R)_n$ is a group of formula $$(XN(CHR_1)_m)_p$$

where p is 3, 4, 5 or 6, each m is 2, 3 or 4, each $R_1$ is a hydrogen atom, a hydrophilic group, or a site-directed group, and each X is a group $R_1$ or a metal coordinating group, with however one carbon or nitrogen attached $R_1$ group providing a bond to the linker moiety.

7. A process as claimed in claim 6 wherein in said chelating agent $Ch(R)_n$ is a DO3A or DOTA residue.

8. A process as claimed in claim 1 wherein said chelating agent is selected from the group consisting of AE-DO3A-cholesteryl carbamate, DO3A-succinyl-PE, DO3A-glutaryl-PE, DO3A-DOBA, DO3A-DOmBA, DO3A-DOoBA, DO3A-DOIA, DO3A-HOBA, DO3A-OOBA and AE-DO3A-dodecenyl-PE.

9. A process as claimed claim 1 wherein said liposomes comprise a phospholipid liposome membrane forming material.

10. A process as claimed in 1 wherein said metal ion is a paramagnetic metal ion.

11. A process as claimed in 1 containing a further chelate of a diagnostically or therapeutically effective metal ion.

12. A process as claimed in claim 11 wherein said further chelate is disposed in the liposome core.

13. A process as claimed in claim 12 containing a gadolinum chelate of said chelating agent and a water soluble, hydrophilic dysprosium chelate as said further chelate.

14. A process as claimed in claim 11 wherein said further chelate is a chelate of a heavy metal cluster.

15. In a method of generating an enhanced image of a human or non-human body comprising parenterally administering a contrast effective amount of a contrast agent to said body and generating an image of at least part of said body, the improvement comprising administering as said contrast agent a liposomal agent according to claim 1.

16. A process as claimed in claim 1, wherein said liposomes comprise a hydrogenated phospholipid liposome membrane forming material.

* * * * *